United States Patent
Bierl et al.

(10) Patent No.: US 6,872,364 B2
(45) Date of Patent: Mar. 29, 2005

(54) APPARATUS FOR ENDOTHERMIC REACTIONS OF ORGANIC COMPOUNDS

(75) Inventors: Thomas W. Bierl, West Chester, PA (US); Vincent A. Durante, West Chester, PA (US); Lawrence H. Finkel, Wayne, PA (US); Daniel E. Resasco, Norman, OK (US)

(73) Assignee: Sunoco, Inc. (R&M), Philadelphia, PA (US)

(*) Notice: Subject to any disclaimer, the term of this patent is extended or adjusted under 35 U.S.C. 154(b) by 277 days.

(21) Appl. No.: 10/331,367

(22) Filed: Dec. 30, 2002

(65) Prior Publication Data

US 2003/0091485 A1 May 15, 2003

Related U.S. Application Data

(60) Division of application No. 08/278,782, filed on Jul. 22, 1994, now Pat. No. 6,525,232, which is a continuation-in-part of application No. 07/874,499, filed on Apr. 27, 1992, now Pat. No. 5,439,859.

(30) Foreign Application Priority Data

Apr. 20, 1993 (CA) .............................. 2094766
Apr. 27, 1993 (JP) .......................... 122069/93

(51) Int. Cl.$^7$ .......................... F27B 15/14; C07C 5/393
(52) U.S. Cl. ...................... 422/139; 422/142; 422/144; 422/145; 422/147
(58) Field of Search ................................ 422/139, 142, 422/144, 145, 147; 585/440, 444, 443

(56) References Cited

U.S. PATENT DOCUMENTS 3,894,110 A * 7/1975 Drehman .................... 585/660
4,435,607 A * 3/1984 Imai ............................ 585/443
4,788,371 A * 11/1988 Imai et al. ................... 585/443
4,806,624 A * 2/1989 Herber et al. ................ 585/440
4,902,849 A * 2/1990 McKay et al. .............. 585/660
5,124,500 A * 6/1992 Clark et al. ................. 585/655
5,430,209 A * 7/1995 Agaskar et al. ............. 585/315
5,439,859 A * 8/1995 Durante et al. ............... 502/66

* cited by examiner

Primary Examiner—N. Bhat
(74) Attorney, Agent, or Firm—Robert A. Koons, Jr.; Matthew P. McWilliams; Buchanan Ingersoll PC

(57) ABSTRACT

An apparatus for conducting an endothermic reaction of an organic' compound in the presence of molecular hydrogen and of multicomponent solids is described. The process of operating the apparatus comprises contacting the compound with a solid catalyst for the endothermic reaction and a hydrogen oxidizing solid reagent intermixed with the solid catalyst. Organic products of the endothermic reaction are produced, with evolution of molecular hydrogen. The solid catalyst becomes gradually deactivated by formation of carbonaceous deposits thereon. The evolved hydrogen undergoes an exothermic reaction with the hydrogen oxidizing solid reagent to form a reduction product which comprises deactivated hydrogen oxidizing solid reagent. The deactivated solid catalyst is reactivated by combustion of carbonaceous deposits thereon and the deactivated hydrogen oxidizing solid reagent is reactivated by contacting the reagent with an oxidizing agent in the absence of substantial quantities of hydrogen and in the absence of substantial quantities of organic compounds other than those on the surface of the reagent. The apparatus provides an endothermic reaction which is carried out in the presence of a fluidized bed of catalyst and in the presence of particles of granular hydrogen oxidizing solid reagent which move downwardly through the fluidized catalyst bed, and in which the solid catalyst and solid reagent are separated prior to reactivation thereof in separate reactivation zones.

27 Claims, 1 Drawing Sheet

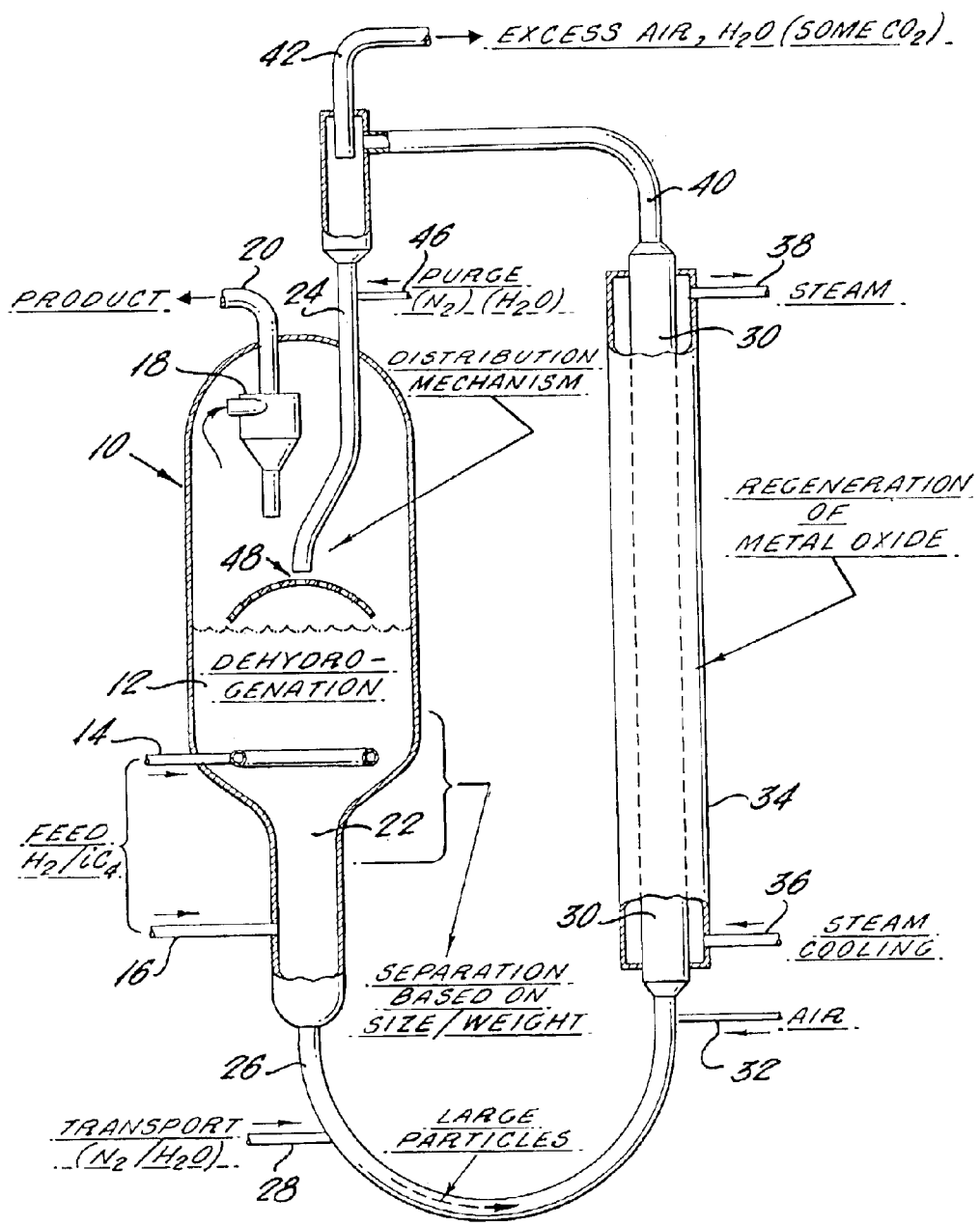

APPARATUS FOR ENDOTHERMIC REACTIONS OF ORGANIC COMPOUNDS

This application is a divisional of application Ser. No. 08/278,782 filed Jul. 22, 1994, now U.S. Pat. No. 6,525,232 which is a continuation-in-part of application Ser. No. 07/874,499 filed Apr. 27, 1992, now U.S. Pat. No. 5,439,859.

BACKGROUND AND PRIOR ART

Endothermic chemical conversions of hydrocarbons and other reactants have been extensively practiced in the prior art. The large investment capital requirements and operating costs associated with such endothermic processes are often related to poor selectivity and low conversion typical of those processes, or to the heat requirements of the processes. Such processes are usually ultimately limited in conversion by an unfavorable position of equilibrium. It is desirable therefore to favorably change the equilibrium by continuous removal of one of the reaction products, and to provide heat required for the process by the conduct of an exothermic reaction simultaneously with the endothermic reaction within the same reactor train. The present invention provides a selective process with improved conversion and consequent lower installation and operating costs while also providing major benefits associated with in situ heat generation and equilibrium shift to achieve higher single-pass conversion.

Some of the commercially used endothermic processes of the prior art use adiabatic reactors, with the resulting disadvantage that the requisite reactor size to approach equilibrium conversion becomes quite large due, to the rapid deceleration of the reaction as the reaction mixture progresses through the bed of catalyst and the temperature drops with increasing conversion of the reaction mixture. An isothermal reactor would require less volume to achieve an equivalent conversion. The present invention makes it possible to conduct endothermic reactions while avoiding the disadvantages of adiabatic reactors.

It has been proposed to conduct endothermic dehydrogenation processes in the presence of oxygen in order to react the hydrogen produced in the dehydrogenation with oxygen to provide a continuous shift of the equilibrium to higher levels and to provide heat for endothermic reaction. However, a practical problem associated with endothermic processes which are conducted in the presence of oxygen in order to oxidize: product hydrogen in situ is that introduction of oxygen which has not been previously diluted with inert gas into the reactor may cause the production of oxygen-fuel mixtures within the bounds of the combustion envelope at temperatures above the autoignition temperature. This may lead to unselective combustion of desired hydrocarbon products or to explosion in an extreme case.

To mix oxygen with hydrocarbons safely in a packed bed requires a large expense. To avoid bulk mixing of oxygen and hydrocarbons, a hydrogen combustion catalyst in the form of a porous ceramic monolith honeycomb, in which oxygen is diffused through the pores of the monolith and the hydrocarbon stream is passed through the tubular channels of the honeycomb over a selective hydrogen combustion catalyst, might be used. In such a system, oxygen and hydrogen would not mix in the bulk except at the interface over the catalyst where selective combustion of hydrogen occurs. This design ameliorates the safety concerns but introduces a heat transfer problem. To effectively transfer heat from the hydrogen combustion zone into the catalyst beds in which the endothermic dehydrogenation reaction proceeds, high wall temperatures are required which may exceed the temperature at which rapid thermal coking of the feed occurs. This is a problem common to all the commercial dehydrogenation processes which use a packed bed reactor for dehydrogenation and not just those which rely on in situ hydrogen combustion to provide heat. But even if hydrogen is oxidized in situ to make the overall process thermoneutral, unless the exothermic combustion process can be conducted in the same zone as the endothermic dehydrogenation, heat transfer limitations may limit efficiency. The present invention provides a way to avoid heat transfer problems while achieving advantages of the use of a porous honeycomb catalyst whether such honeycomb catalyst is used or not.

Imai in U.S. Pat. Nos. 4,435,607 and 4,788,371 discloses dehydrogenation of alkanes in processes which include selective hydrogen combustion by oxygen, but have the disadvantage of adding oxygen to a zone in which there is either a high concentration of combustible organic compounds necessitating a high concentration of diluent such as steam to prevent combustion of organic compounds.

Clark et al U.S. Pat. No. 5,124,500 discloses a process for the removal of hydrogen from a mixture of hydrogen and organic compounds by selective reaction of the hydrogen with a molecular sieve containing a reducible metal cation, and discloses one type of material that could be used in the reactor design embodiment of the present invention. No specific reactor concept is disclosed by Clark, et al, nor any concept of the importance or difficulty of efficiently using the exotherm associated with hydrogen oxidation to provide heat for the dehydrogenation.

DESCRIPTION OF THE INVENTION

The process according to the invention is a process for conducting an endothermic reaction of a liquid or vaporous organic compound in the presence of molecular hydrogen and of multicomponent solids including a solid catalyst for the endothermic reaction and a hydrogen oxidizing solid reagent to react with the hydrogen. The solid catalyst and the hydrogen oxidizing solid reagent are intermixed, either as separate particles or incorporated within the same particle. The organic compound and the hydrogen are contacted with the catalyst and the hydrogen oxidizing reagent under conditions to produce organic products of the endothermic reaction and to react hydrogen by an exothermic reaction with the hydrogen oxidizing reagent to form deactivated hydrogen oxidizing reagent and water vapor. The deactivated hydrogen oxidizing reagent is reactivated by contact with an oxidizing agent in the absence of substantial quantities of hydrogen and in the absence of substantial quantities of organic compounds other than those on the surface of the deactivated reagent.

In one embodiment of the invention, the endothermic reaction is a dehydrogenation reaction of an alkane to an olefin or of an alkyl-substituted aromatic compound to an aromatic compound substituted with an unsaturated side chain. Preferably, the endothermic reaction is conducted in a fluidized bed and the solid granular hydrogen oxidizing reagent is passed downwardly onto the fluidized bed as raining solids. In one embodiment of the invention, hydrogen is cofed to the endothermic reaction zone with the hydrogen oxidizing reagent. The dehydrogenation is preferably conducted at a temperature in the range from about 500 to about 700° C. and a pressure in the range from about 0 to about 100 psig.

In one embodiment, deactivated catalyst and hydrogen oxidizing reagent are not separated prior to reactivating and are reactivated in a common reactivation zone. In another embodiment, deactivated catalyst and deactivated hydrogen oxidizing reagent are separated prior to reactivating and are reactivated in separate reactivation zones.

In one embodiment of the latter manner of conducting the process, the deactivated catalyst has lesser density or smaller size than the deactivated hydrogen oxidizing reagent and the deactivated catalyst and deactivated reagent pass from the endothermic reaction zone into a separation zone. In the separation zone, a gravity separation is effected, and deactivated catalyst is withdrawn from an upper portion of the separation zone and deactivated hydrogen oxidizing agent is withdrawn from a lower portion of the separation zone.

In another embodiment wherein deactivated catalyst and deactivated hydrogen oxidation reagent are separated prior to reactivation, the deactivated catalyst has different magnetic properties from the deactivated hydrogen oxidizing reagent and is separated therefrom by differentially attracting either the deactivated catalyst or the deactivated reagent to a magnet.

Advantages of the Process of the Invention

The process of the invention has advantages over prior art processes for conducting endothermic reactions in that the process of the invention conducts the endothermic reaction in the same reaction zone in which an exothermic oxidation of hydrogen is conducted. Where the process of the invention is a dehydrogenation process, it has the advantages, as compared with the process of Imai above, of less explosion hazard, greater selectivity for oxidation of only the hydrogen component rather than the hydrocarbon component, and elimination of dilutes to control combustion of organics; and the advantages as compared with Clark above, of providing improved reactor design which efficiently uses the exotherm associated with hydrogen oxidation. The invention also provides novel processes using particular selective hydrogen oxidizing agents.

Hydrogen Oxidizing Solid Reagent

In the dehydrogenation embodiment of the invention, organic compounds are dehydrogenated in the presence of a selective and regenerable hydrogen oxidizing reagent which stoichiometrically, as opposed to catalytically, removes hydrogen as it is produced within a dehydrogenation zone. No molecular oxygen is introduced into the dehydrogenation zone. The hydrogen oxidizing reagent functions as an oxygen transfer reagent, that is, as a reagent which transfers oxygen from the reagent to hydrogen, to form either water or a hydroxide, MOH, on the surface of the solid reagent, where the original reagent is MO.

Preferably the hydrogen oxidizing reagent used in the process of the invention has the formula $MO_x$ where M comprises a metal selected from the group consisting of iron, manganese, barium, calcium, samarium, praseodymium, ruthenium, tin, lead, germanium or bismuth, and where x varies depending on the stoichiometry of the specific oxide. Examples of such reagents are praseodymium oxides, barium peroxide, iron oxides, manganese oxides and samarium-calcium oxide mixtures.

The hydrogen oxidizing reagents include reducible metal oxides, metal complexes of organic ligands, or other inorganic compounds with or without metal atoms but which contain oxygen. These compounds are relatively inert under dehydrogenation reaction conditions and can be reactivated with a source of oxygen. The reactivation conditions are chosen so as not to destroy the organic ligands, if they are present. Among the useful compositions are those metal oxides and doped metal oxides which promote the dehydrodimerization of methane, and which are readily reducible by hydrogen but not as easily reducible by hydrocarbons as by hydrogen. The choice of hydrogen oxidizing reagent depends in part on the nature of the hydrocarbon feed to be dehydrogenated and on the products thereof, and on the reaction and reoxidation conditions. Supported or unsupported iron, manganese and praseodymium oxides and salmarium-calcium oxide mixtures are useful hydrogen oxidizing reagents at conditions typically useful to convert isobutane to isobutene. Iron oxide in the form of magnetite is usually preferred to hematite. For lower temperature operation, compounds such as supported cis-dioxo-bis-octafluorobipyridin ruthenium (VI) tetrafluoroborate may be a useful reagent. Other reagents as described in the literature of methane coupling, such as disclosed for example in B. D. Sokolovskii, Catalysis Today, 14 (1992) 331, are useful as hydrogen oxidizing reagents according to the invention, as well as tin phosphate and tin pyrophosphate and the corresponding lead, germanium or bismuth phosphate compounds.

Use of Hydrogen Oxidizing Solid Reagents

The hydrogen oxidizing solid reagents used in the process of the invention are those compounds and compositions which selectively react with hydrogen in admixture with hydrocarbons, and which can be reactivated by reoxidation. The reagents are readily reduced by dihydrogen but not by the organic compounds which comprise the feed or dehydrogenated organic products under the process conditions. Water can be formed either as a direct result of the reaction between hydrogen and the reagent, equations (3) and (4), while the hydrogen oxidizing reagent is in the reaction zone where hydrogen is produced by dehydrogenation, or in a second step as the reagent is oxidized, equations (1) and (2), in a reactivation zone in a step subsequent to the initial reaction with hydrogen:

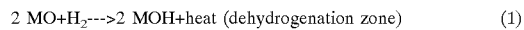
2 MO+H$_2$--->2 MOH+heat (dehydrogenation zone)   (1)

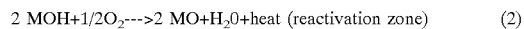
2 MOH+1/2O$_2$--->2 MO+H$_2$0+heat (reactivation zone)   (2)

or

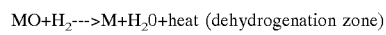
MO+H$_2$--->M+H$_2$0+heat (dehydrogenation zone)

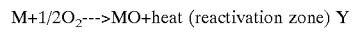
M+1/2O$_2$--->MO+heat (reactivation zone) Y

In reaction (1), the hydrogen oxidizing reagent, MO, is reduced by H2 generated in the dehydrogenation reaction to form MOH, and in reaction (2), MO is reactivated by oxidation of MOH. In reaction (3), MO is reduced by H$_2$ to produce a reduced form of the reagent, M, and in reaction (3), M is reoxidized to MO. In reaction (2), water is formed as a product of the reoxidation of MOH to MO. In reaction (3), water is formed as a product of the reduction of MO to M.

Dehydrogenation Catalysts

Dehydrogenation catalysts which may be used in the process of the invention include catalysts known in the art for such reactions, and catalysts which are the subject of related inventions. Prior art dehydrogenation catalysts include chromium supported on alumina, the catalysts disclosed in Miller U.S. Pat. No. 4,726,216, the Pt, tin, cesium and alumina catalyst disclosed in Imai et al U.S. Pat. No. 4,788,371, the dehydrogenation catalysts disclosed in Miller U.S. Pat. No. 4,726,216 and in Herber U.S. Pat. No. 4,806,624, potassium promoted iron catalyst as disclosed in Imai et al, The Principle of Styro Plus, AICHE Nat. Mtg. New Orleans, March 1988, Reprint 64a; Process Engineering (London), (1988), 69, 17. When the reaction zone is a fluidized bed, the dehydrogenation catalyst may be spray dried to fluidizable particle sizes, about 60–80 micron average particle size, and appropriate particle densities. Appropriate binders and textural promoters may be added as known in the art, to produce particles with satisfactory physical properties once formed by spray drying.

Typical Embodiment of the Invention

In a typical embodiment of the process of the invention, a dehydrogenatable hydrocarbon such as isobutane is contacted with a solid dehydrogenation catalyst such as nickel cesium alumina and with a solid hydrogen oxidizing reagent such as an iron oxide plus tin phosphate mixture under dehydrogenation conditions such as 600° C. and atmospheric pressure with space velocity GHSV of 885 $hr^{-1}$. The particles of dehydrogenation catalyst are separate from the particles of hydrogen oxidizing reagent interspersed therein in a common reaction zone. The hydrocarbon feed is dehydrogenated, forming an unsaturated hydrocarbon such as isobutylene, and hydrogen. The hydrogen reacts with the hydrogen oxidizing reagent, reducing components of the latter to a lower oxidation state, and forming water as a byproduct. Unsaturated hydrocarbon is removed, as a product of the process and the reduced hydrogen oxidizing reagent particles are optionally separated from the dehydrogenation catalyst particles and removed to a hydrogen oxidizing reagent reactivation zone in which they are reoxidized to their former oxidation state. The dehydrogenation catalyst particles are separately transported to a catalyst reactivation zone in which coke is burned off the catalyst and then returned to the dehydrogenation reactor and mixed with the reactivated hydrogen oxidizing reagent prior to contacting hydrocarbon feed to the dehydrogenation reaction. Optionally the dehydrogenation catalyst particles and the hydrogen oxidizing reagent particles can be transported together to a common reactivation zone without prior separation.

Carbonaceous deposits form in the dehydrogenation reactor on both the dehydrogenation catalyst and the hydrogen oxidizing reagent. The carbonaceous deposits on the hydrogen oxidizing reagent, and on any dehydrogenation catalyst that may be removed from the dehydrogenation reactor along with the hydrogen oxidizing reagent, are removed by combustion during the reoxidation of the hydrogen removal reagent.

Separation of Dehydrogenation Catalyst and Hydrogen Oxidizing Reagent

In the dehydrogenation embodiment of the invention, the reaction is conducted with the dehydrogenation catalyst in a highly subdivided, or powdered, form, and the hydrogen removal reagent in the form of larger and/or denser particles than the particles of the dehydrogenation catalyst, and following the dehydrogenation and oxidation of the resulting hydrogen, a gravity separation is effected between the larger and/or denser hydrogen oxidizing reagent particles from the smaller and/or less dense particles of the dehydrogenation catalyst. The larger and/or denser phase from the separation is removed from the reactor for reoxidation as described above, and the smaller and/or less dense phase from the separation may be separately removed from the reactor. Alternatively, magnetic separation may be used to remove an iron-containing hydrogen oxidizing reagent from the dehydrogenation catalyst. Cyclone separators may also be used to separate the dehydrogenation catalyst particles from the hydrogen oxidizing reagent particles of a different particle size or density prior to separate reagent reactivation and catalyst reactivation steps of the process.

Reactivation of Dehydrogenation Catalyst and Hydrogen Oxidizing Reagent

The dehydrogenation catalyst removed from the separation zone is reactivated in a dehydrogenation catalyst reactivation zone, in which carbonaceous deposits are burned from the dehydrogenation catalyst, under conditions which may be the same as or differ from those in the reactivation of the hydrogen oxidizing reagent. Any reduced hydrogen oxidizing reagent which may be carried into the dehydrogenation catalyst reactivation zone with the dehydrogenation catalyst is reoxidized therein to its former oxidation state and relieved of carbonaceous deposits thereon under the combustion conditions prevailing in the catalyst reactivation zone. The conditions in the catalyst reactivation zone are those which are effective for reactivating a mixture of dehydrogenation catalyst and hydrogen oxidizing reagent predominating in dehydrogenation catalyst, whereas the conditions in the hydrogen oxidizing reagent reactivation zone are those which are effective for reoxidizing a mixture of hydrogen oxidizing reagent and dehydrogenation catalyst predominating in hydrogen oxidizing reagent. The conditions maybe approximately the same in the catalyst reactivation zone and in the reagent reactivation zone, and may even be conducted in the same reactivation zone, but it is preferred to conduct the catalyst reactivation and reagent reactivation in separate zones under conditions in each which are particularly effective for the catalyst reactivation and hydrogen oxidizing reagent reactivation respectively.

Process Heat

The reactivation of the hydrogen oxidizing reagent is conducted in a separate vessel or a separate zone from the zone in which dehydrogenation and reaction of hydrogen with hydrogen oxidizing reagent takes place. Heat may be generated both in the dehydrogenation zone itself as a result of the initial reaction with hydrogen and in the reactivation zone. Heat produced in the latter case is transported by the solid particles back to the dehydrogenation zone to help heat balance the system. The amount of heat produced in the dehydrogenation zone can be throttled by adjusting the relative rate per unit reactor volume of dehydrogenation relative to the rate of hydrogen burning, or heat can be removed by known heat transfer techniques. The hydrogen oxidation reactions are less sensitive to extremes of temperature than the dehydrogenation reactions. The relative rates of the respective reactions are conveniently adjusted by varying the rate of introduction of the hydrogen removal reagent. In one embodiment of the invention, heat consumption by the endothermic dehydrogenation and heat production by the exothermic hydrogen oxidation are balanced to achieve process thermoneutrality. In such cases when alkanes are the substrates for dehydrogenation to monoalkenes, roughly one half of the produced hydrogen is required to be oxidized to bring the system to thermoneutrality. The required amount of hydrogen burning is lessened to the extent that usually undesired exothermic hydrogenolysis reactions may occur in the dehydrogenation zone. The hydrogen oxidizing reagent also can be used advantageously without regard to the heat balance of the process. Even more hydrogen can be removed than dictated by the heat balance requirements to facilitate further shifting of the position of equilibrium toward products. Any excess heat produced in such case can be removed by known heat transfer techniques and provided as a utility to other processes.

The process of the invention provides high per-pass conversions and in situ heat to the process by removing all or part of the product hydrogen as it is formed in the dehydrogenation zone. This is effected by addition of a selective stoichiometric hydrogen oxidizing reagent which oxidizes the hydrogen exothermally to continuously shift the dehydrogenation equilibrium to a more favorable position and consequently increase the limiting conversion of the process, and to provide heat to offset the heat demand of the concurrent dehydrogenation reaction. Non-selective combustion of hydrocarbons and potential explosion hazards are avoided in the process of the invention, in contrast to processes in which molecular oxygen is introduced into the same reactor as that which contains a high concentration of combustible organic compounds. In order to conduct the process of the invention in a heat balanced isothermal reactor, a circulating fluidized bed reactor may be used.

Particles Containing Granular Solids of Two or More Kinds

According to one embodiment of the invention, granular solids of two or more kinds are incorporated in particles containing solids of each kind. For example, for use in a dehydrogenation process, the particles may contain both a dehydrogenation catalyst and a hydrogen oxidizing reagent. The dehydrogenation catalyst in the particles effects dehydrogenation of the organic compound feed to the process. The hydrogen oxidizing reagent in the particles reacts with hydrogen produced in the dehydrogenation and is reduced to a lower oxidation state. Carbonaceous deposits form on the particles as a result of the dehydrogenation conditions in the reactor, and these deposits are removed by combustion in a separate reactivation zone in which the activity of the dehydrogenation catalyst is at least partially restored, and the reduced hydrogen oxidizing reagent is simultaneously reoxidized to a higher oxidation state under the conditions prevailing in the reactivation zone. The reactivated dehydrogenation catalyst and the reactivized hydrogen oxidizing reagent are returned to the dehydrogenation reactor to contact additional feed material. This embodiment is a particular instance of operation according to the invention wherein the reactivation of the catalyst and the reactivation of the hydrogen oxidizing reagent are effected in a common reactivation zone. In the embodiments of the invention in which the dehydrogenation catalyst particles are distinct from the hydrogen oxidizing reagent particles, the reactivation of the catalyst and the reactivation of the hydrogen oxidizing reagent may be effected in the same reactivation zone or in separate reactivation zones.

In a circulating fluidized bed system, with combustive reactivation of the dehydrogenation catalyst, one embodiment of the invention provides a hydrogen oxidizing reagent which is capable of reactivation together with the dehydrogenation catalyst. In another embodiment, a hydrogen oxidizing reagent is used which is reactivated separately from the dehydrogenation catalyst, for example because of disparate rates of regeneration of the two materials, or in order to stage the heat release during reactivation, or to decouple the cycle timing for the reactivation of the two materials; in this embodiment :a raining solids fluidized bed reactor is provided which permits separation of the dehydrogenation catalyst component from the hydrogen oxidizing component, in order to allow for separate reactivation of the two materials. Where the lifetime of the dehydrogenation catalyst between regenerations is relatively long, it may be desirable to circulate the hydrogen oxidizing reagent to a separate reactivation zone more frequently than the cycle time for reactivation of the dehydrogenation catalyst, or it may be necessary or desirable to reactivate the hydrogen oxidizing reagent under different reactivation conditions from the dehydrogenation catalyst reactivation conditions.

Raining Solids Circulating Fluidized Bed Reactor

A fluidized bed reactor operated in a nearly isothermal mode is a preferred reactor configuration for use in the process of the invention. In one embodiment of the invention, a circulating fluidized bed reactor is provided which contains a distribution mechanism to disperse a superimposed free fall of granular solids comprising the hydrogen oxidizing reagent. Unlike the dehydrogenation catalyst, the freely falling solid is not fluidized by the fluidizing gas flow because those particles are either larger or more dense than the fluidizable dehydrogenation catalyst particles. The freely falling particles which contain the hydrogen oxidizing reagent react with hydrogen as they fall through the dehydrogenation zone and collect at the bottom of the reaction vessel, and classification of the hydrogen oxidizing reagent from the dehydrogenation catalyst component is controlled. From the bottom of the reaction vessel, the now-spent hydrogen oxidizing reagent is circulated to a reactivator vessel for reoxidation in the presence of an oxygen-containing gas and eventually recirculated to the dehydrogenation zone.

Applicability of the Invention

According to one embodiment of the invention, organic compounds are dehydrogenated with the simultaneous selective conversion of at least a portion of the byproduct dihydrogen to an oxidized product, either water or a reduced form of an added reagent such as MO in equations (1) and (3) above. Such operation is to be distinguished from mechanistically coupled oxidative dehydrogenation as discussed below. The invention potentially provides more favorable process economics than those of current commercially practiced processes. The invention may be advantageously applied to new processes or to existing processes for the dehydrogenation of alkanes such as the Snam-Progetti-Yarsintez Process, which uses a fluidized bed reactor as used in one of the embodiments of this invention.

The process of the invention is applicable as a step in any desired dehydrogenation reaction in which hydrogen is generated as a product and for which equilibrium does not lie substantially on the side of products, or in any desired dehydrogenation reaction which consumes heat. Oxidative dehydrogenations in which molecular hydrogen is not generated as an intermediate in situ or as a final reaction product do not usually, but may sometimes, benefit. The process of the invention may be useful in dehydrogenation of alkanes to alkenes, alkadienes or alkynes such as the conversion of isobutane to isobutene or the conversion of ethyl benzene to styrene; the preparation of aldehydes or ketones from alcohols; the preparation of alkanes or aromatics by the dehydrogenative coupling of lower alkanes or lower aromatics such as the conversion of methane to ethane or isobutane to 2,2,3,3-tetramethylbutane or the conversion of benzene to biphenyl; the conversion of naphthenes (hydroaromatics) to aromatics such as tetrahydronaphthalene to naphthalene; the cycloaromatization of alkanes such as heptane to toluene when limited by equilibrium; the dehydrogenation of monoalkenes to dienes such as cis-butene-2 to butadiene; and other processes for the preparation of intermediate or specialty chemicals.

Apparatus for Contacting Gas or Vapor with Granular Solids

The invention comprises in one embodiment apparatus for conducting an endothermic reaction of a fluid, that is, in vapor or liquid state, organic compound in the presence of molecular hydrogen and of multicomponent solids. The apparatus of the invention comprises (a) means for contacting the organic compound with a fluidized bed of granular solid particles of a catalyst for the endothermic reaction and with granular solid particles of a hydrogen oxidizing reagent intermixed with the fluidized bed, to produce fluid reaction products, deactivated particles of the catalyst having carbonaceous deposits thereon and deactivated particles of the hydrogen oxidizing reagent, (b) means for separating the particles of the catalyst from the particles of the reagent, and (c) means for separately reactivating the deactivated particles of the catalyst by combustion of the carbonaceous deposits and the deactivated hydrogen oxidizing solid reagent by contact of the reagent with an oxidizing agent.

In one embodiment of the apparatus according to the invention, the means for separating catalyst from reagent comprise means for effecting gravity separation of the particles of the reagent from the particles of the catalyst. In another embodiment, the means for separating comprise means for effecting magnetic separation of the particles of the reagent from the particles of the catalyst.

The Drawing

The FIGURE illustrates a typical embodiment of process and apparatus according to the invention. Shown in the FIGURE is a catalytic dehydrogenation reactor 10, containing a fluidized bed 12 of fluidizable solid dehydrogenation catalyst having about 60–80 micron average particle size, feed inlets 14 and 16, cyclone 18, product outlet 20, solids separation zone 22, hydrogen oxidizing reagent inlet 24, hydrogen oxidizing reagent outlet and transport line 26, transport gas inlet 28, reoxidation zone 30, air inlet 32, cooling jacket 34, steam inlet 36, steam outlet 38, reoxidized oxygen transfer reagent outlet 40, vapor and gas outlet 42, purge inlet 46 and distribution mechanism 48.

In operation, hydrogen oxidizing reagent, for example a compound, MO where M comprises a metal such as iron, circulates from reactor 10 through transport line 26, reactivation zone 30, reactivated hydrogen oxidizing reagent outlet 40 from the reactivator, hydrogen oxidizing reagent inlet 24 to the reactor, and back through distribution mechanism 48 into reactor 10, where it mixes with the fluidized dehydrogenation catalyst in fluidized bed 12 and contacts, along with the dehydrogenation catalyst, a feed comprising hydrogen and hydrocarbon" for example isobutane, introduced through feed inlets 14 and 16. The dehydrogenation catalyst catalyzes dehydrogenation of the feed, with generation of hydrogen, and the hydrogen oxidizing reagent reacts with hydrogen to form the compound MOH where M is a metal such as iron. Dehydrogenated product passes through cyclone 18, where catalyst particles are separated therefrom and returned to the catalyst bed 12, and is removed through product line 20. By gravity, the particles of the hydrogen oxidizing reagent, which are larger and/or denser than the "particles of the dehydrogenation catalyst, are concentrated in the lower portion of separation zone 22. In reoxidation zone 30, the hydrogen oxidizing reagent is contacted with air introduced through line 32, which reacts with the MOH of the hydrogen oxidizing reagent particles to form MO and water and generate heat. Some carbon dioxide is also formed from carbonaceous material on the hydrogen oxidizing reagent. The water and carbon dioxide are removed, along with excess air, from reoxidation zone 30 through outlet 40.

The invention claimed is:

1. An apparatus for conducting a continuous endothermic reaction of a fluid organic compound in the presence of molecular hydrogen and multi-component solids wherein said multi-component solids comprise a solid catalyst for said endothermic reaction and a hydrogen oxidizing solid reagent intermixed with said solid catalyst, said apparatus comprising:

a first reactor for contacting said compound with said multi-component solids to produce organic products and deactivated multi-component solids; and at least one second reactor in continuous sequence with said first reactor for reactivating said deactivated multi-component solids and circulating at least one portion of said reactivated multi-component solids to said first reactor for providing a continuous source of solid catalyst and hydrogen oxidizing solid reagent to sustain said endothermic reaction without interruption of the flow of said fluid organic compound undergoing endothermic reaction and for providing a portion of heat required for said endothermic reaction.

2. The apparatus of claim 1 wherein said first reactor is a fluidized bed.

3. The apparatus of claim 1 further comprising a distribution mechanism near the top of said first reactor for distributing said reactivated multi-component solids in said first reactor.

4. The apparatus of claim 1 wherein said hydrogen oxidizing solid reagent comprises reducible metal oxides.

5. The apparatus of claim 4 wherein said reducible metal oxides are selected from the group consisting of iron oxides, manganese oxides, and samarium-calcium oxide mixtures.

6. The apparatus of claim 1 wherein said hydrogen oxidizing solid reagent comprises cis-dioxo-octafuorobipyridin ruthenium (VI) tetrafluoroborate.

7. The apparatus of claim 1 wherein said hydrogen oxidizing solid reagent is selected from the group consisting of tin, lead, germanium and bismuth phosphates or pyrophosphates.

8. The apparatus of claim 1 further comprising at least one separator for separating and removing said deactivated multi-component solids from said first reactor.

9. The apparatus of claim 8 wherein said separation comprises gravity, magnetic, and cyclone separation.

10. The apparatus of claim 1 wherein said at least one second reactor comprises two reactors for reactivating said solid catalyst and said hydrogen oxidizing solid reagent.

11. The apparatus of claim 1 wherein said solid catalyst and said hydrogen oxidizing solid reagent are incorporated into single solid particles to form said multi-component solids.

12. An apparatus for conducting a continuous endothermic reaction of a fluid organic compound in the presence of molecular hydrogen and multi-component solids wherein said multi-component solids comprise a solid catalyst for said endothermic reaction and a hydrogen oxidizing solid reagent incorporated into single solid particles, said apparatus comprising:

a first reactor for contacting said compound with said multi-component solids, to produce organic products and deactivated multi-component solids; and a second reactor in continuous sequence with said first reactor for reactivating said deactivated multi-component solids and circulating at least one portion of said reactivated multi-component solids to said first reactor for providing a continuous source of solid catalyst and hydrogen oxidizing solid reagent to sustain said endothermic reaction without interruption of the flow of said fluid organic compound undergoing endothermic reaction and for providing a portion of heat required for said endothermic reaction.

13. The apparatus of claim 12 wherein said first reactor is a fluidized bed.

14. The apparatus of claim 12 wherein said hydrogen oxidizing solid reagent comprises reducible metal oxides.

15. The apparatus of claim 14 wherein said reducible metal oxides are selected from the group consisting of iron oxides, manganese oxides, and samarium-calcium oxide mixtures.

16. The apparatus of claim 12 wherein said hydrogen oxidizing solid reagent comprises cis-dioxo-octafuorobipyridin ruthenium (VI) tetrafluoroborate.

17. The apparatus of claim 12 wherein said hydrogen oxidizing solid reagent is selected from the group consisting of tin, lead, germanium and bismuth phosphates or pyrophosphates.

18. An apparatus for conducting an endothermic reaction of a fluid organic compound in the presence of molecular hydrogen and of multi-component solids which comprises (a) contacting said compound with a solid catalyst for said endothermic reaction and a hydrogen oxidizing solid reagent intermixed with said solid catalyst, thereby (i) to produce organic products of said endothermic reaction and molecular hydrogen, (ii) to form deactivated solid catalyst having carbonaceous deposits thereupon, (iii) to react said hydrogen by an exothermic reaction with said hydrogen oxidizing solid reagent and (iv) to form a reduction product comprising deactivated hydrogen oxidizing solid reagent, (b) reactivating said deactivated solid catalyst by combustion of said carbonaceous deposits and (c) reactivating said deactivated hydrogen oxidizing solid reagent by contacting said reagent with an oxidizing agent in the absence of substantial quantities of hydrogen and in the absence of substantial quantities of organic compounds other than those on the surface of the reagent, said apparatus comprising:

a first reactor comprising a fluidized bed reactor for contacting said compound with said multi-component solids which comprise said solid catalyst and said hydrogen oxidizing solid reagent and wherein said multi-component solids form an intermixed bed of particles for said endothermic reaction to produce said organic products, said deactivated solid catalyst, and said deactivated hydrogen oxidizing solid reagent; and at least one second reactor in continuous sequence with said first reactor for reactivating said deactivated solid catalyst and said deactivated hydrogen oxidizing solid reagent and circulating said reactivated solid catalyst and said reactivated hydrogen oxidizing solid reagent to said first reactor for providing a continuous source of active solid catalyst and hydrogen oxidizing reagent solid to sustain said endothermic reaction without interruption of the flow of said fluid organic compound undergoing endothermic reaction and for providing a portion of heat required for said endothermic reaction.

19. The apparatus of claim 18 further comprising a distribution mechanism near the top of said first reactor for distributing said reactivated solid catalyst and said reactivated hydrogen oxidizing solid reagent in said first reactor.

20. The apparatus of claim 18 wherein said hydrogen oxidizing solid reagent comprises reducible metal oxides.

21. The apparatus of claim 20 wherein said reducible metal oxides are selected from the group consisting of iron oxides, manganese oxides, and samarium-calcium oxide mixtures.

22. The apparatus of claim 18 wherein said hydrogen oxidizing solid reagent comprises cis-dioxo-octafuorobipyridin ruthenium (VI) tetrafluoroborate.

23. The apparatus of claim 18 wherein said hydrogen oxidizing solid reagent is selected from the group consisting of tin, lead, germanium and bismuth phosphates or pyrophosphates.

24. The apparatus of claim 18 further comprising at least one separator for separating and removing said deactivated solid catalyst and said deactivated hydrogen oxidizing solid reagent from said first reactor.

25. The apparatus of claim 24 wherein said separation comprises gravity, magnetic, and cyclone separation.

26. The apparatus of claim 18 wherein said at least one second reactor comprises two reactors for separately reactivating said deactivated solid catalyst and said deactivated hydrogen oxidizing solid reagent.

27. The apparatus of claim 18 wherein said multi-component solids comprise said solid catalyst and said hydrogen oxidizing solid reagent incorporated into single solid particles.

* * * * *